United States Patent
Mankodi et al.

(10) Patent No.: US 10,057,675 B2
(45) Date of Patent: Aug. 21, 2018

(54) INTEGRATION OF SENSORS INTO EARPHONES

(71) Applicant: Bose Corporation, Framingham, MA (US)

(72) Inventors: Harsh Anilkant Mankodi, Brighton, MA (US); Kyle DeCubellis, South Boston, MA (US); Marko Orescanin, Framingham, MA (US); Michael D. Ting, Boston, MA (US); Jonathan D. Turner, Arlington, MA (US)

(73) Assignee: Bose Corporation, Framingham, MA (US)

( * ) Notice: Subject to any disclaimer, the term of this patent is extended or adjusted under 35 U.S.C. 154(b) by 0 days.

(21) Appl. No.: 14/812,672

(22) Filed: Jul. 29, 2015

(65) Prior Publication Data

US 2017/0034615 A1    Feb. 2, 2017

(51) Int. Cl.
*H04R 1/10*    (2006.01)
*A61B 5/00*    (2006.01)

(52) U.S. Cl.
CPC ......... *H04R 1/1091* (2013.01); *A61B 5/0059* (2013.01); *A61B 5/6817* (2013.01); *A61B 5/6843* (2013.01); *H04R 1/1016* (2013.01); *A61B 5/6815* (2013.01); *H04R 1/105* (2013.01); *H04R 1/1041* (2013.01)

(58) Field of Classification Search
CPC .... H04R 1/1091; H04R 1/1016; H04R 1/105; H04R 1/1066; H04R 1/10; H04R 25/652; H04R 25/656
USPC .......................................... 381/74, 380, 384
See application file for complete search history.

(56) References Cited

U.S. PATENT DOCUMENTS

| 8,308,641 | B2 * | 11/2012 | Moroney, III | ......... G16H 40/63 600/301 |
| 8,419,637 | B2 * | 4/2013 | Nielsen | ................... A61B 5/02 600/301 |
| 8,647,270 | B2 | 2/2014 | LeBoeuf et al. | |
| 8,700,111 | B2 | 4/2014 | LeBoeuf et al. | |

(Continued)

FOREIGN PATENT DOCUMENTS

| WO | 2007004083 A1 | 1/2007 | |
| WO | WO 2007004083 A1 * | 1/2007 | ............... A61B 5/02 |

OTHER PUBLICATIONS

International Search Report and Written Opinion dated Nov. 9, 2016 for International application No. PCT/US2016/044530.

*Primary Examiner* — Davetta W Goins
*Assistant Examiner* — Oyesola C Ojo

(57) ABSTRACT

An in-ear earphone includes a body shaped to fit in the wearer's ear, a nozzle extending from the body towards the ear canal of the wearer's ear, the nozzle including an acoustic passage to conduct sound waves to the ear canal of the wearer, an ear canal sealing structure extending from the nozzle, and a sensor coupled to the nozzle. The sealing structure includes a thin sheet of material forming a hollow shape surrounding the nozzle and sensor, and the body, nozzle, sealing structure, and sensor are arranged such that when the earphone is located in the wearer's ear, the sensor faces the tragus of the ear, and the sealing structure simultaneously forms an acoustic seal to the entrance to the ear canal and provides optical coupling between the sensor and the tragus with minimal air gaps between the sensor, the sealing structure, and the tragus.

18 Claims, 5 Drawing Sheets

(56) References Cited

U.S. PATENT DOCUMENTS

| | | | |
|---|---|---|---|
| 8,788,002 B2* | 7/2014 | LeBoeuf | A61B 5/0077 600/310 |
| 8,929,582 B2 | 1/2015 | Silvestri et al. | |
| 2009/0069645 A1* | 3/2009 | Nielsen | A61B 5/02 600/301 |
| 2009/0088611 A1 | 4/2009 | Buschmann | |
| 2010/0217098 A1* | 8/2010 | LeBoeuf | A61B 5/00 600/301 |
| 2011/0182457 A1* | 7/2011 | Tung | H04R 1/1041 381/380 |
| 2012/0197093 A1* | 8/2012 | LeBoeuf | G16H 40/63 600/301 |
| 2013/0131519 A1* | 5/2013 | LeBoeuf | A61B 5/0077 600/476 |
| 2013/0218022 A1* | 8/2013 | Larsen | A61B 5/01 600/474 |
| 2013/0336495 A1* | 12/2013 | Burgett | H04R 1/1091 381/74 |
| 2014/0046192 A1* | 2/2014 | Mullin | H05K 13/00 600/474 |
| 2015/0257662 A1* | 9/2015 | Lee | A61B 5/02427 600/323 |
| 2016/0249133 A1* | 8/2016 | Sorensen | H04R 1/105 |

* cited by examiner

INTEGRATION OF SENSORS INTO EARPHONES

BACKGROUND

This specification describes designs for integrating sensors into earphones.

SUMMARY

In general, in one aspect, an in-ear earphone includes a body shaped to fit in the wearer's ear, a nozzle extending from the body towards the ear canal of the wearer's ear, the nozzle including an acoustic passage to conduct sound waves to the ear canal of the wearer, an ear canal sealing structure extending from the nozzle, and a sensor coupled to the nozzle. The sealing structure includes a thin sheet of material forming a hollow shape surrounding the nozzle and sensor, and the body, nozzle, sealing structure, and sensor are arranged such that when the earphone is located in the wearer's ear, the sensor faces the tragus of the ear, and the sealing structure simultaneously forms an acoustic seal to the entrance to the ear canal and provides optical coupling between the sensor and the tragus with minimal air gaps between the sensor, the sealing structure, and the tragus.

Implementations may include one or more of the following, in any combination. The sealing structure may have an outer surface that contacts skin of the wearer's ear, and an inner surface that contacts the sensor module, the outer surface and the inner surface being polished such that light passing through the sealing structure is not scattered or reflected by the outer and inner surfaces. The body and the sealing structure may be formed of a single piece, the entire surface of which may be polished. The sensor may include an emitter that emits light at a predetermined wavelength, and the sealing structure may be formed of a soft plastic that transmits light having the predetermined wavelength and attenuates light having at least some other wavelengths. The body and the sealing structure may be formed of a single piece, the entirety of which transmits light having the predetermined wavelength and attenuates light having at least some other wavelengths.

The sensor may include an emitter that emits light at first and second predetermined wavelengths, with the first wavelength being one of infrared or ultraviolet, and the second wavelength being typically visible to humans, and the earphone controls the sensor to emit light at the second wavelength when the earphone is not located in an ear. The sensor may include an emitter that emits light and a contact sensor, and the sensor may be configured to only emit light when the contact sensor is activated. The sensor may contribute to the formation of the acoustic seal by applying pressure to the sealing structure and, through the sealing structure, to ear tissue in the vicinity of the ear where the sealing structure forms the seal. When the earphone is placed in an ear, the sensor may be aligned with the tragus of the ear, and the concha may press against the body, which presses the sensor and the sealing structure against the tragus, such that the sealing structure is in contact with both the sensor and the tragus, and the sealing structure seals the entrance to the ear canal.

In general, in one aspect, an in-ear earphone includes an ear-canal sealing structure configured to form an acoustic seal to a wearer's ear canal, and a sensor. The sensor contributes to the formation of the acoustic seal by applying pressure to the sealing structure and, through the sealing structure, to ear tissue, in the vicinity of the ear where the sealing structure forms the seal.

In general, in one aspect, a sensor assembly for use with an in-ear earphone includes a sensor circuit having one or more apertures through which light is radiated or collected, a housing surrounding the sensor circuit, and an ear interface for the in-ear earphone. The ear interface includes a body shaped to fit in the lower concha of a wearer's ear, a nozzle extending from the body, the nozzle including an acoustic passage to conduct sound waves from the earphone to the ear canal of the wearer, and an ear canal sealing structure extending from the nozzle, including a thin layer of material forming a hollow shape surrounding the nozzle and sensor circuit. The sensor assembly also includes electronic terminals for coupling the sensor circuit to a circuit external to the sensor assembly, and a mounting feature for mechanically coupling the sensor assembly to a nozzle of an earphone.

Implementations may include one or more of the following, in any combination. When the sensor assembly is mounted on an earphone which is placed in an ear, the sealing structure may be in contact with both the sensor and the ear, the sealing structure simultaneously forming an acoustic seal to the entrance to the ear canal and providing optical coupling between the sensor and the ear. The body, nozzle, sealing structure, and apertures may be arranged such that when the sensor assembly is mounted on an earphone which is placed in an ear, the apertures face the tragus of the ear, and the sealing structure simultaneously forms an acoustic seal to the entrance to the ear canal and provides optical coupling between the apertures and the tragus with no air gaps between the apertures, the sealing structure, and the tragus.

In general, in one aspect, an in-ear earphone includes a body shaped to fit in the lower concha of a wearer's ear, a nozzle extending from the body towards the ear canal of the wearer's ear, the nozzle including an acoustic passage to conduct sound waves to the ear canal of a user, an ear canal sealing structure extending from the nozzle, and a sensor coupled to the nozzle. The sealing structure includes a thin layer of material forming a hollow, generally frusto-conical shape surrounding the nozzle and sensor, and when the earphone is placed in the wearer's ear, the sensor is aligned with the tragus of the ear, the concha presses against the body which presses the sensor and the sealing structure against the tragus, such that the sealing structure is in contact with both the sensor and the tragus, and the sealing structure seals the entrance to the ear canal.

Other features, objects, and advantages will become apparent from the following detailed description, when read in connection with the following drawing, in which:

These figures show an in-ear earphone with an ear interface that are designed to fit in the left ear. An earphone that is designed to fit in the right ear may be a mirror image of the earphone depicted, and operates according to the same principles, and is not specifically described herein. Similarly, an earphone and ear interface may be symmetric, such that they fit in either ear, and do not depart significantly from what is depicted.

DETAILED DESCRIPTION

Figure 1:
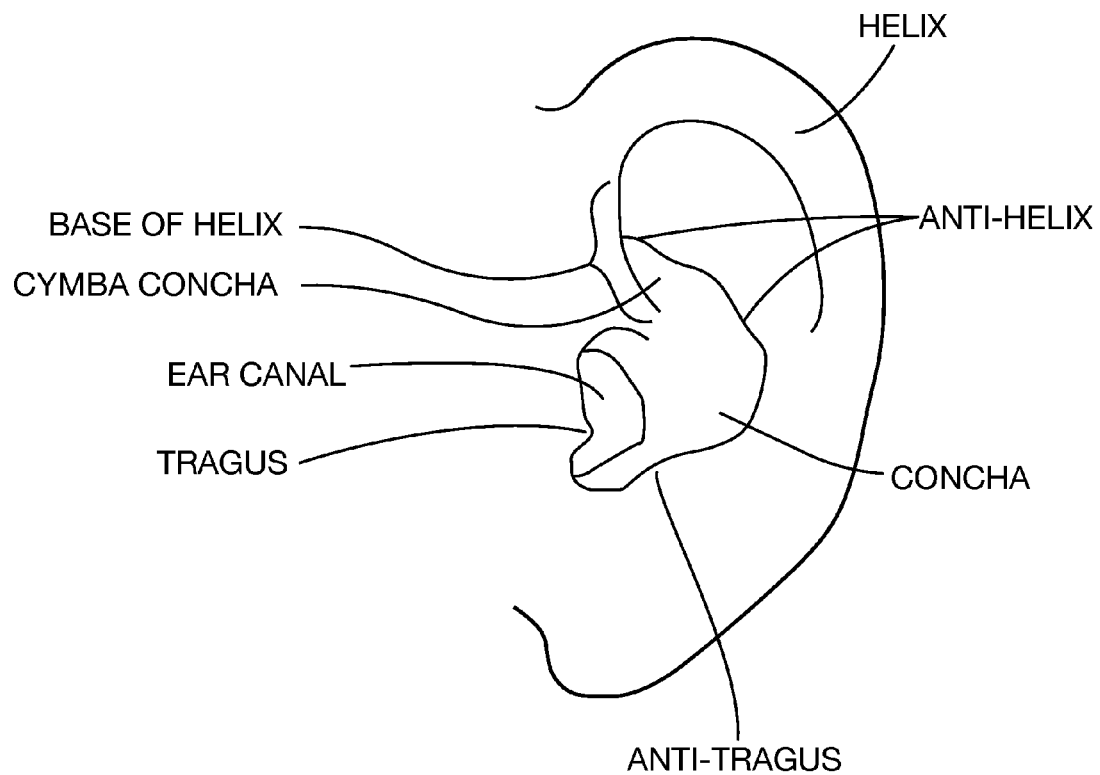
FIG. 1 is a view of the lateral surface of the human ear.

FIG. 1 shows the lateral surface of a human left ear, with some features identified. There are many different ear sizes and geometries. Some ears have additional features that are not shown in FIG. 1. Some ears lack some of the features that are shown in FIG. 1. Some features may be more or less prominent than are shown in FIG. 1.

Figure 2:
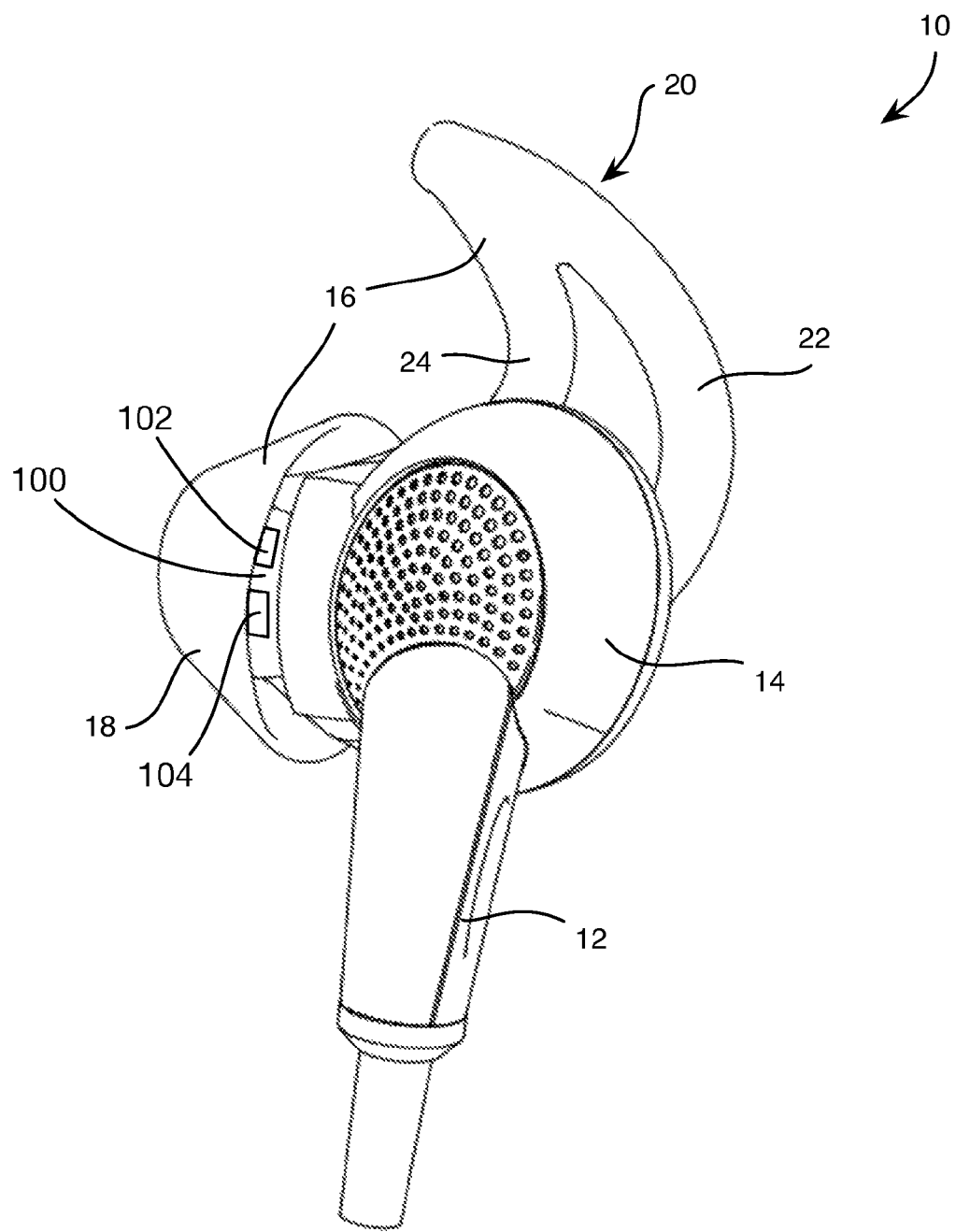
FIG. 2 is a perspective view of an earphone with an ear interface.

FIG. 2 shows an earphone 10. The earphone 10 may include a stem 12 for positioning cabling and the like, an acoustic driver module 14, and an ear interface 16, sometimes called an ear tip. Some earphones may lack the stem 12 but may include electronics modules (not shown) for wireless communication with external devices. Other earphones may lack the stem and the acoustic driver module and may function as passive earplugs. The ear interface 16 includes a positioning and retaining structure 20, which in this example includes an outer leg 22 and an inner leg 24, but may take various other forms. The ear interface also includes a sealing structure 18. Not seen in this view of the earphone, the ear interface also includes a cushion body that fits into the concha of the user's ear.

In addition to the acoustic and ergonomic components, the earphone 10 includes a sensor module 100. The sensor module includes an emitter 102 and a detector 104, both positioned at or near the outside surface of the sensor module, so that they will be positioned close to the skin of the ear. Although shown with the emitter 102 vertically above the detector 104, various orientations may be used. Light from the emitter passes into the ear tissue, where is reflected back to be detected by the detector. Physiological conditions to be detected influence the reflected light, and can therefore be measured from the light received at the detector. Additional sensor technology may also be included, such as a capacitive, conductive, or mechanical touch sensors used to turn on the optical sensor when the earphone is located in the ear or to provide additional physiological information.

In operation, the earphone 10 is placed in the ear and is oriented and held in place by positioning and retaining structure 20 and other portions of the earphone. It is desirable to place the earphone in the ear so that it is oriented properly, so that it is stable (that is, stays in the ear), so that it is comfortable, for some applications so that it provides significant passive attenuation of ambient noise, and so that the sensor module remains in good contact with the skin of the ear. The use of the positioning and retaining structure shown to provide stability and proper orientation is described more completely in U.S. Pat. No. 8,249,287, incorporated herein by reference in its entirety. The use of the sealing structure 18 to provide passive attenuation and control of the acoustic response of the earphone is described in U.S. Pat. No. 8,682,001, incorporated herein by reference in its entirety.

Figure 3:
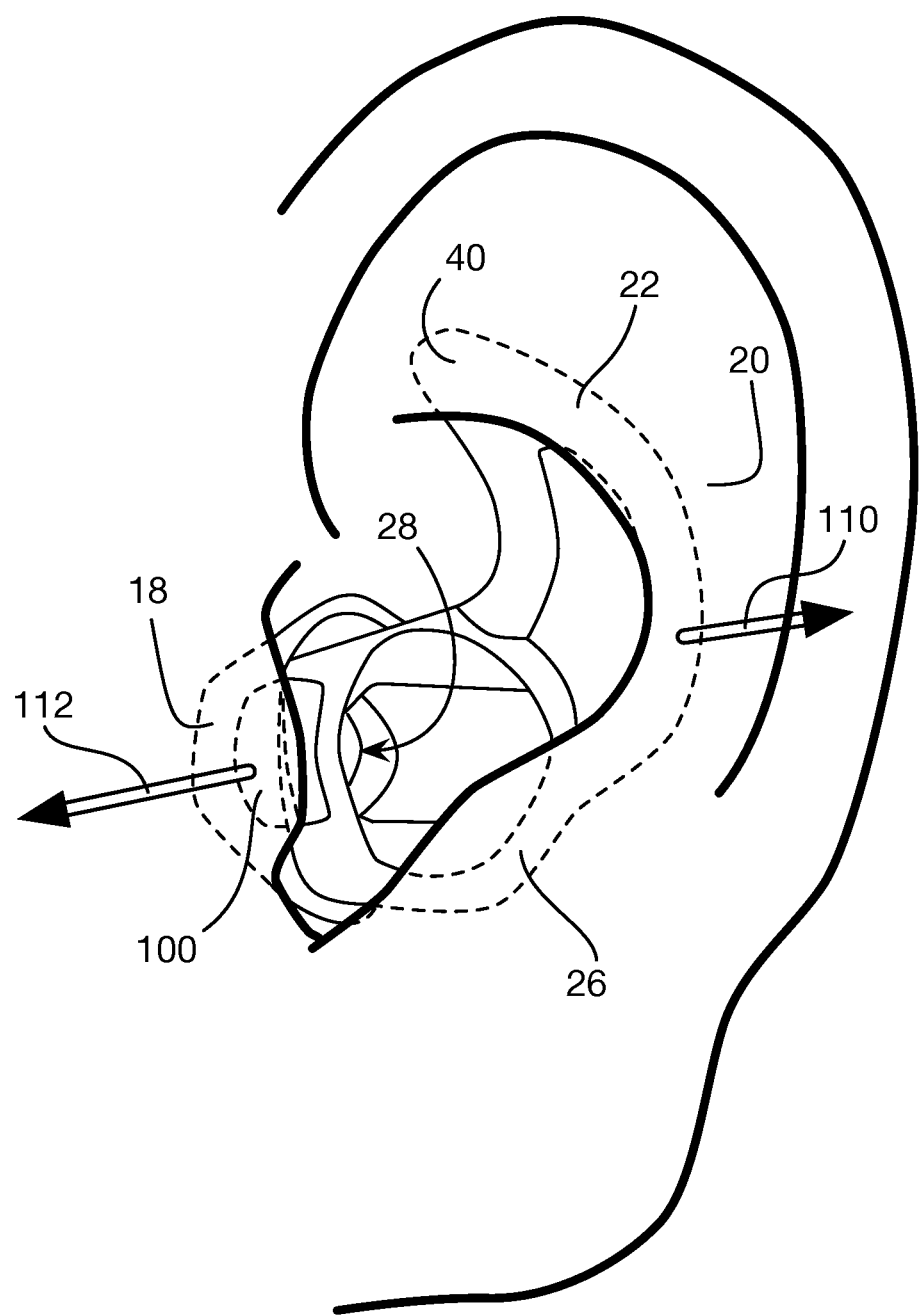
FIG. 3 is a lateral view of the ear interface of FIG. 2 in a human ear.

FIG. 3 shows the ear interface 16 and sensor module 100 in an ear with the rest of the earphone omitted for clarity. The ear interface 16 includes a cushion body 26, mentioned above, which in turn includes a passageway 28 to conduct sound waves radiated by an acoustic driver in the acoustic driver module 14 (FIG. 2) to the ear canal. Extending from the ear interface 16 is the positioning and retaining structure 20 that holds the earphone in position, without significant contribution from the portions of the ear interface that engage the ear canal and without any structure external to the ear interface. The positioning and retaining structure 20 is on the opposite side of the earphone from the sensor module 100, such that as the positioning and retaining structure presses into the anti-helix in one direction, arrow 110, it results in the sensor being pressed in substantially the opposite direction, arrow 112, against the tragus. Thus, the positioning and retaining structure not only holds the earphone in the ear, it holds the sensor against the skin so that a reliable optical signal can be read from the skin.

When fitting the earphone to the ear, it may be rotated to cause the end 40 and outer leg 22 of the positioning and retaining structure 20 to engage the cymba concha region and seat beneath the anti-helix. When the body 26 and positioning and retaining structure 20 are in place, the positioning and retaining structure and/or body contact the ear of most people in at least two, and in many people more, of several ways: the outer edge of the outer leg 22 contacts the anti-helix at the rear of the concha; the end 40 of the positioning and retaining structure 20 is underneath the anti-helix; portions of the outer leg 22 or body 26 or both are underneath the anti-tragus; and the sealing structure 18 contacts at the entrance to the ear canal under the tragus. The two or more points of contact hold the earphone in position, providing greater stability. All of these also serve to press the sensor module, through the sealing structure, against the tragus. The distributing of the force, and the compliance of the portions of the body and the outer leg that contact the ear, lessens pressure on the ear, providing a more comfortable fit, even with the sensor added to the earphone.

Figure 4:
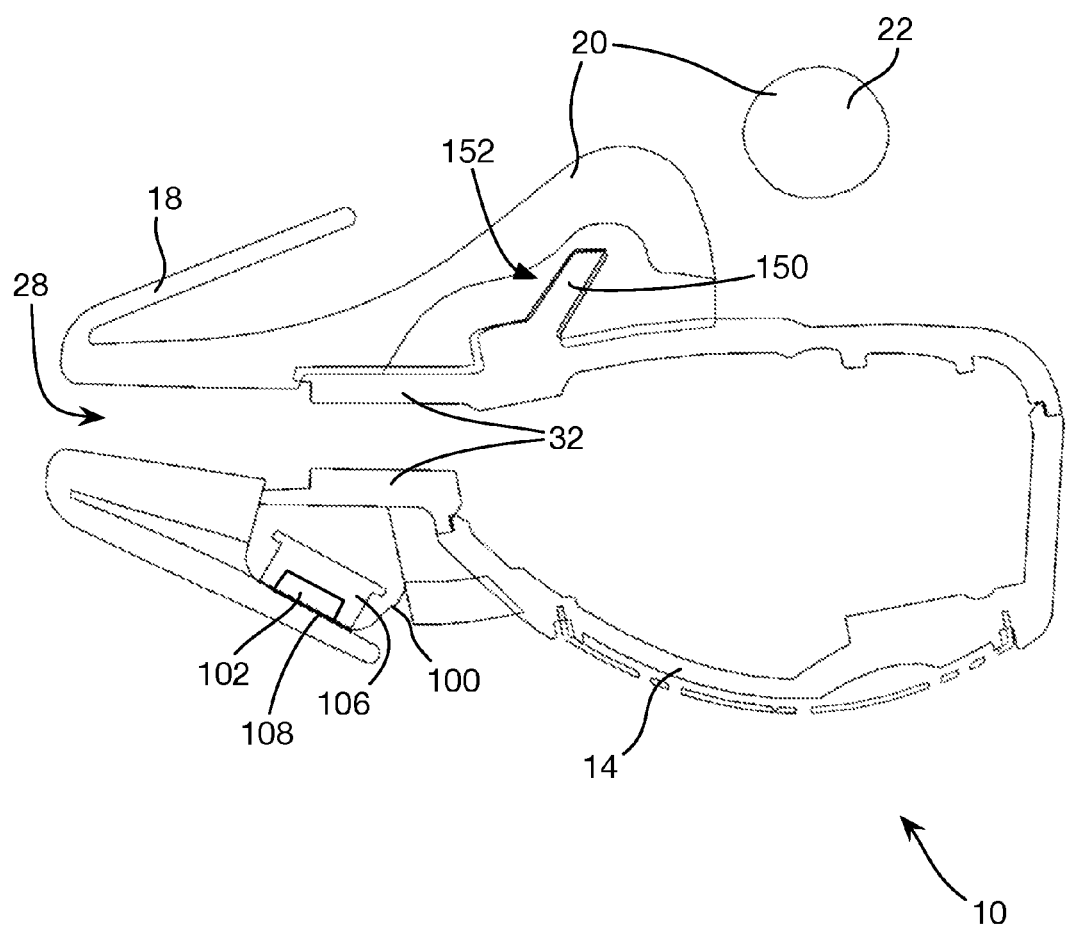
FIG. 4 is a cross-sectional view of the earphone and ear interface of FIG. 2.

As shown in FIG. 4, a cross-section of the earphone 10, the acoustic driver module 14 includes a nozzle 32 that couples to the passageway 28 in the ear interface, connecting the driver (not shown) to the ear canal. In some examples, this provides a more uniform acoustic response than a fully compliant passageway might. The sensor module 100 is attached to the outside of the nozzle 32, under the sealing structure 18. The sealing structure 18 is modified from one designed for use without the sensor, such as that described in U.S. Pat. No. 8,737,669, mentioned above. In particular, and as shown in FIG. 4, the area of the sealing structure directly over the sensor module is flattened slightly, bringing it closer to the sensor, and lengthened, so that it fully covers the sensor module. The ear tip is retained on the ear bud by fitting a tab 150 into a slot 152.

When the earphone is placed in the ear, the sealing structure is trapped between the sensor and the tissue of the ear. The resulting position of the sealing structure 18 relative to the sensor module 100 is shown in FIG. 4 as being flat against the sensor module 100. This may be the resting position of the sealing structure, but in other examples, the sealing structure may be shaped to have a small air gap between itself and the sensor module; once inserted to the ear, it is pressed against the sensor as in FIG. 4. In addition to forming a seal to the ear canal, trapping the sealing structure between the sensor and the ear also eliminates any air gap between the sensor and the tissue of the ear. Being on the opposite side of the earphone from the positioning and retaining structure of the ear interface, the sensor module presses against the sealing structure, pressing it against the ear tissue at the tragus, simultaneously maintaining the acoustic seal and assuring a high-quality optical interface for the sensor.

As shown in FIG. 2, the sensor module 100 includes an emitter 102 and a detector 104, both positioned at or near the outside surface of the sensor module, so that they will be pressed against the sealing structure (only one of the sensor or emitter is shown in the side view used for FIG. 4). They may be enclosed on the back by a standard integrated circuit package 106, and they may be protected on top by a cover 108, which may be, for example, glass, polycarbonate, or a coating of epoxy or other light-transmissive material. Light from the emitter passes through the sealing structure 18 and into the ear tissue, where is reflected back to pass through the sealing structure again and be detected by the detector. As noted above, physiological conditions to be detected influence the reflected light. When we refer to "light", we include infrared and ultraviolet, as well as visible light, any of which may be used in a particular sensing application.

Depending on the wavelength of light used by the sensor, additional modifications may be made to the sealing structure 18 to assure a high quality signal is conducted through it. The surfaces of the sealing structure 18 (or the entire ear interface 16, depending on the methods used) may be polished, allowing the light to enter and leave the material with minimal disruption (e.g., reflection or scattering at the interface). In addition, specific dye may be used, as described in U.S. patent application Ser. No. 14/672,459, filed Mar. 30, 2015, and incorporated here by reference, to tune the optical transmission properties of the ear interface to pass light at the frequencies of interest and, preferably, also attenuate or block light at other frequencies. This may take the form of a narrow band-pass behavior, transmitting only light at the wavelength in use, or a long-pass or short-pass behavior, blocking light on one side or the other of the spectrum from the wavelength in use. The entire ear interface may be dyed, or only the sealing structure, or only the part of the sealing structure over the sensor module, depending on the molding process used and the desired aesthetics of the ear interface.

In some examples, the emitter can be configured to generate light at a number of frequencies, including both visible and invisible (i.e., infrared or ultraviolet) light. While light in a non-visible range may be useful for the sensing application, the visible light may be used to provide a user interface. That is, when removed from the ear, the visible light may be used to signal that the sensor is operating, or other information about the earphone, such as what state it is in, or the level of battery charge. The visible light may be generated all the time, or only when the earphone is removed from the ear, if it is not needed for the sensing application. Conversely, the invisible light used for sensing may be generated all the time, or only when the earphone is in the ear, to conserve power or to avoid exposing the user's eyes to ultraviolet or infrared light, if that is a concern. Detection that the earphone is not in the ear may come from the detector, as the reflected light will be absent or greatly attenuated, or from other sensors, as noted above. In the case of a noise-reducing headphone with a feedback microphone, audio signals detected by the feedback microphone can also be used to determine whether the earphone is in the ear or not.

Figure 5:
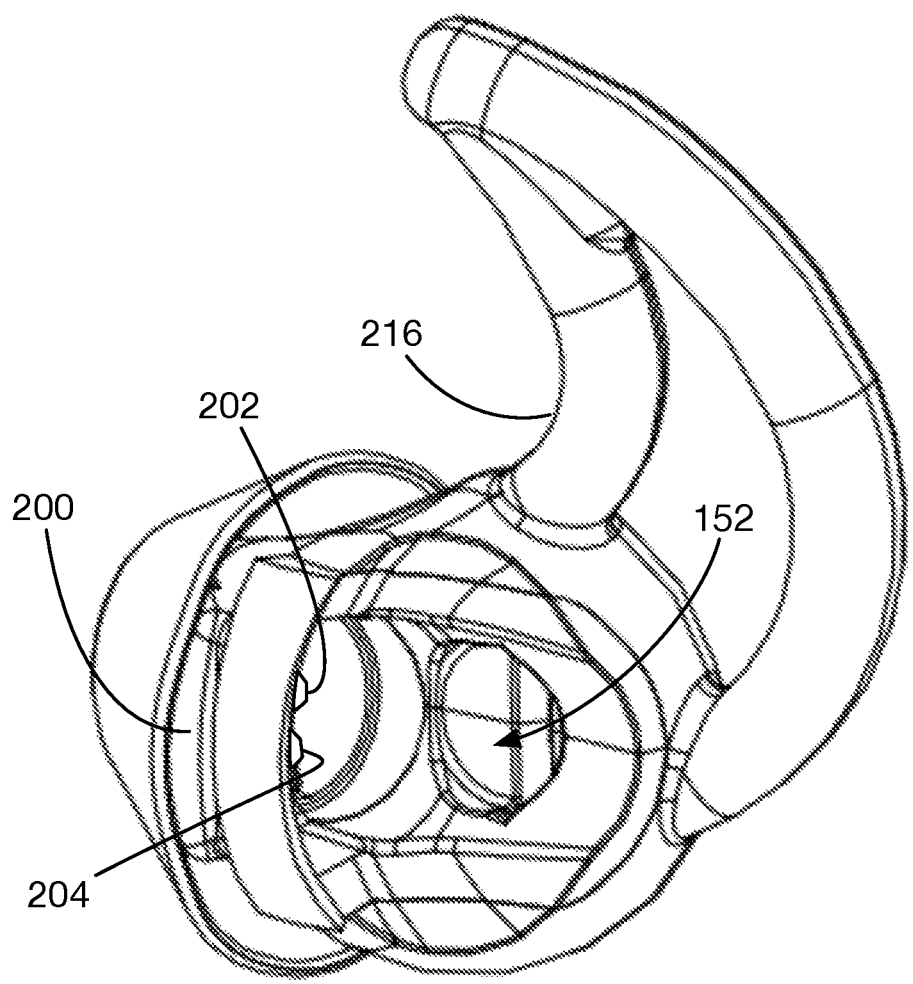
FIG. 5 is a perspective view of an ear interface with integrated sensors.

In another example, as shown in FIG. 5, a sensor module 200 is permanently installed in an ear interface 216, rather than on the housing of the earphone (not shown). Electrical contacts 202, 204 on the sensor module align with corresponding contacts on the surface of the earphone housing, so that power and data can be exchanged between the sensor module and electronics in or on the earphone. Such a design may, among other things, allow for a more customized positioning of the sensor within ear interfaces of different sizes, or for more reliable coupling of the sensor to the ear tissue.

Numerous uses of and departures from the specific apparatus and techniques disclosed herein may be made without departing from the inventive concepts. Consequently, the invention is to be construed as embracing each and every novel feature and novel combination of features disclosed herein and limited only by the spirit and scope of the appended claims.

What is claimed is:

1. An in-ear earphone, comprising:
a body shaped to fit in the wearer's ear;
a nozzle extending from the body towards the ear canal of the wearer's ear, the nozzle including an acoustic passage to conduct sound waves to the ear canal of the wearer;
an ear canal sealing structure extending from the nozzle; and
a sensor coupled to the nozzle;
wherein
the sealing structure comprises a thin sheet of material forming an open hollow shape surrounding the nozzle and sensor, extending over and spaced apart from at least the sensor when the earphone is not seated in the wearer's ear; and
the body, nozzle, sealing structure, and sensor are arranged such that when the earphone is located in the wearer's ear, the sensor faces the tragus of the ear, and the sealing structure simultaneously forms an acoustic seal to the entrance to the ear canal and contacts the sensor to provide optical coupling between the sensor and the tragus with minimal air gaps between the sensor, the sealing structure, and the tragus.

2. The earphone of claim 1, wherein the sealing structure has an outer surface that contacts skin of the wearer's ear, and an inner surface that contacts the sensor module, the outer surface and the inner surface being polished such that light passing through the sealing structure is not scattered or reflected by the outer and inner surfaces.

3. The earphone of claim 2, wherein the body and the sealing structure are formed of a single piece, the entire surface of which is polished.

4. The earphone of claim 1, wherein
the sensor includes an emitter that emits light at a predetermined wavelength, and
the sealing structure is formed of a soft plastic that transmits light having the predetermined wavelength and attenuates light having at least some other wavelengths.

5. The earphone of claim 4, wherein the body and the sealing structure are formed of a single piece, the entirety of which transmits light having the predetermined wavelength and attenuates light having at least some other wavelengths.

6. An in-ear earphone, comprising:
a body shaped to fit in the wearer's ear;
a nozzle extending from the body towards the ear canal of the wearer's ear, the nozzle including an acoustic passage to conduct sound waves to the ear canal of the wearer;
an ear canal sealing structure extending from the nozzle; and
a sensor coupled to the nozzle;
wherein
the sealing structure comprises a thin sheet of material forming an open hollow shape surrounding the nozzle and sensor when the earphone is not seated in the wearer's ear; and
the body, nozzle, sealing structure, and sensor are arranged such that when the earphone is located in the wearer's ear, the sensor faces the tragus of the ear, and the sealing structure simultaneously forms an acoustic seal to the entrance to the ear canal and provides optical coupling between the sensor and the tragus with minimal air gaps between the sensor, the sealing structure, and the tragus, and the sensor includes an emitter that emits light at first and second predetermined wavelengths, wherein the first wavelength is one of infrared or ultraviolet, and the second wavelength is typically visible to humans, the earphone controls the sensor to emit light at the first wavelength when the earphone is located in an ear, and the earphone controls the sensor to emit light at the second wavelength when the earphone is not located in an ear.

7. The earphone of claim 1, wherein the sensor includes an emitter that emits light and a contact sensor, and the sensor is configured to only emit light when the contact sensor is activated.

8. The earphone of claim 1, wherein the sensor contributes to the formation of the acoustic seal by applying pressure to the sealing structure and, through the sealing structure, to ear tissue in the vicinity of the ear where the sealing structure forms the seal.

9. The earphone of claim 1, wherein when the earphone is placed in an ear, the sensor is aligned with the tragus of the ear;

the concha presses against the body which thereby presses the sensor and the sealing structure against the tragus, such that the sealing structure is in contact with both the sensor and the tragus; and the sealing structure seals the entrance to the ear canal.

10. An in-ear earphone, comprising:

an ear-canal sealing structure configured to form an acoustic seal to a wearer's ear canal, comprising a thin sheet of material forming an open hollow shape surrounding the nozzle and sensor, extending over and spaced apart from at least the sensor when the earphone is not seated in the wearer's ear; and a sensor;

wherein the sensor contributes to the formation of the acoustic seal by applying pressure to the sealing structure at the point that the sealing structure extends over the sensor and, through the sealing structure, to ear tissue, in the vicinity of the ear where the sealing structure forms the seal.

11. The earphone of claim 10, wherein the sealing structure has an outer surface that contacts skin of the wearer's ear, and an inner surface that contacts the sensor, the outer surface and the inner surface being polished such that light passing through the sealing structure is not scattered or reflected by the outer and inner surfaces.

12. The earphone of claim 10, wherein the sensor includes an emitter that emits light at a predetermined wavelength, and the sealing structure is formed of a soft plastic that transmits light having the predetermined wavelength and attenuates light having at least some other wavelengths.

13. A sensor assembly for use with an in-ear earphone, comprising:

a sensor circuit having one or more apertures through which light is radiated or collected;

a housing surrounding the sensor circuit;

an ear interface for the in-ear earphone, the ear interface comprising:

a body shaped to fit in the lower concha of a wearer's ear;

a nozzle extending from the body, the nozzle including an acoustic passage to conduct sound waves from the earphone to the ear canal of the wearer; and an ear canal sealing structure extending from the nozzle, comprising a thin layer of material forming an open hollow shape surrounding the nozzle and sensor circuit, extending over and spaced apart from at least the sensor when not seated in the wearer's ear, and contacting the sensor to provide optical coupling between the sensor and ear when seated in the wearer's ear;

electrical contacts for coupling the sensor circuit to a circuit external to the sensor assembly; and a mounting feature for mechanically coupling the sensor assembly to a nozzle of an earphone.

14. The sensor assembly of claim 13, wherein when the sensor assembly is mounted on an earphone which is placed in an ear, the sealing structure is in contact with both the sensor and the ear; and the sealing structure simultaneously forms an acoustic seal to the entrance to the ear canal and provides optical coupling between the sensor and the ear.

15. The sensor assembly of claim 13, wherein the body, nozzle, sealing structure, and apertures are arranged such that when the sensor assembly is mounted on an earphone which is placed in an ear, the apertures face the tragus of the ear, and the sealing structure simultaneously forms an acoustic seal to the entrance to the ear canal and provides optical coupling between the apertures and the tragus with no air gaps between the apertures, the sealing structure, and the tragus.

16. The sensor assembly of claim 15, wherein the sealing structure has an outer surface that contacts skin of the wearer's ear, and an inner surface that contacts the sensor, the outer surface and the inner surface being polished such that light passing through the sealing structure is not scattered or reflected by the outer and inner surfaces.

17. The earphone of claim 15, wherein the sensor circuit includes an emitter that emits light at a predetermined wavelength, and the sealing structure is formed of a soft plastic that transmits light having the predetermined wavelength and attenuates light having at least some other wavelengths.

18. An in-ear earphone, comprising:

a body shaped to fit in the lower concha of a wearer's ear;

a nozzle extending from the body towards the ear canal of the wearer's ear, the nozzle including an acoustic passage to conduct sound waves to the ear canal of a user;

an ear canal sealing structure extending from the nozzle; and a sensor coupled to the nozzle;

wherein the sealing structure comprises a thin layer of material forming an open hollow, generally frusto-conical shape surrounding the nozzle and sensor, extending over and spaced apart from at least the sensor when the earphone is not in the wearer's ear; and when the earphone is placed in the wearer's ear, the sensor is aligned with the tragus of the ear;

the concha presses against the body which thereby presses the sensor and the sealing structure against the tragus, such that the sealing structure is in contact with both the sensor and the tragus; and the sealing structure seals the entrance to the ear canal.

\* \* \* \* \*